ABSTRACT
United States Patent [19]

Stover

[11] 4,108,722

[45] Aug. 22, 1978

[54] METHOD FOR THE RESTORATION OF AN UNDERGROUND RESERVOIR

[75] Inventor: Dennis E. Stover, Plano, Tex.

[73] Assignee: Atlantic Richfield Company, Los Angeles, Calif.

[21] Appl. No.: 749,597

[22] Filed: Dec. 10, 1976

[51] Int. Cl.$^2$ ............................................. C12B 1/00
[52] U.S. Cl. ........................................ 195/1; 299/4; 423/17
[58] Field of Search ...................... 195/1, 2, 3 R, 3 H; 299/4, 5; 423/17; 75/101

[56] References Cited

U.S. PATENT DOCUMENTS

| | | | |
|---|---|---|---|
| 2,574,070 | 11/1951 | Strawinski | 195/3 H |
| 2,954,218 | 9/1960 | Dew et al. | 299/4 |
| 3,024,612 | 3/1962 | Ludeman | 299/5 X |
| 3,118,500 | 1/1964 | Maddox et al. | 166/246 |

*Primary Examiner*—R. B. Penland
*Attorney, Agent, or Firm*—Ronnie D. Wilson

[57] ABSTRACT

The present invention relates to a method for the restoring of an underground reservoir subsequent to the solution mining of a mineral from a subterranean formation. More specifically, the invention relates to the introduction of a sulfate reducing bacteria into a subterranean formation to decrease the total dissolved solids level of the reservoir present therein.

6 Claims, No Drawings

METHOD FOR THE RESTORATION OF AN UNDERGROUND RESERVOIR

Generally, known processes for solution mining of a mineral in situ utilize an acid or alkaline leach solution for the dissolution of the mineral. An oxidant is injected into the formation along with the leach solution. The mineral is leached from the formation and recovered from a production well via a pregnant leach solution. Various procedures for recovering the mineral from the pregnant leach solution are well known, such as ion exchange.

The method of the present invention is particularly suitable for an underground reservoir which has been perturbed by the leaching of uranium; however, my invention is not so limited. The following description will be in regard to uranium leached reservoirs; however, it is apparent that it is applicable to reservoirs perturbed during the leaching of other mineral values such as copper, nickel, vanadium, molybdenum, silver, rhenium, and selenium where similar problems are encountered.

An inherent problem of solution mining uranium via an acid or alkaline solution is the dissolving of other soluble ionic species in addition to uranium causing an increase in the level of total dissolved solids (TDS) in the reservoir fluids. Other soluble ionic species include calcium, iron, magnesium, radium, sodium, chloride, molybdenum, selenium, sulfate, and vanadium. Sources of these ions are: calcite, which dissolves to produce calcium and carbonate or bicarbonate ions; molybdenite, which produces molybdate and sulfate; and iron sulfides (marcasite and pyrite), which produce sulfate as well as both soluble and insoluble iron compounds. If such soluble species are not recovered from the pregnant leach solution during operation, they will continue to accumulate throughout the life of the leaching operation, limited only by their respective saturation maximums. The extent of this accumulation is directly measured by analysis of the TDS level of the reservoir fluid.

Primary constituents of the increased TDS level are bicarbonate, carbonate, chloride and sulfate ions. Each can be present in concentrations of several hundred ppm in a perturbed reservoir fluid. The chloride and sulfate species are extremely stable, and hence, resistant to chemical reduction.

At termination of an in situ uranium solution mining operation it is necessary to restore the reservoir fluid to near or at its original conditions for a variety of reasons. Certain of the TDS constituents (contaminants) can be removed via conventional water purification processes. For example, the alkaline metal ions as well as chloride ions can be stripped from the fluid using ion exchange resins; however, the feasibility of such processes is limited by equipment and operating costs. Similarly, sulfate ions can be removed by precipitation of the sulfate ions in an insoluble form, for example, precipitation of insoluble barium sulfate using barium chloride as the precipitating agent. The major drawback to this method is the cost of the precipitating agent. Another restoration scheme would be to pump the contaminated fluid from the reservoir, letting native formation water flow into the contaminated region, and dispose of the contaminated fluid. Studies have shown that more than three times the volume of contaminated fluid must be pumped from the reservoir to insure approaching the original conditions within the contaminated region. The removal of such a potentially large volume of water from an acquifier may not be feasible in many areas. In addition, the removed contaminated fluid must be disposed into deep injection wells or evaporation ponds since state and federal regulatory agencies prohibit the discharge of such waters into surface waters. The costs associated with these two disposal methods are substantial. In the present invention, equipment, material, and operating costs are minimized by use of a bacteria which consumes carbonate and nitrogen species while reducing sulfate to sulfide. The solubility of the sulfide form of many of the cation contaminants is sufficiently low that they precipitate and further reduce the TDS level of the reservoir fluid.

During the course of an in situ uranium solution mining operation two major perturbations are inflicted upon the reservoir. Restoration of a leach reservoir to its original state is contingent upon reversal of these perturbations which are, 1) the change of the reservoir from a reduced to an oxidized state, and 2) the increase of the TDS level of the reservoir from a nominal 1000 ppm to several thousand ppm. The second perturbation is a direct result of the acidization or oxidation leaching process. Therefore, there is needed a method whereby these perturbations are reversed and a leached reservoir restored to its original state for the long term.

Therefore, it is an object of the present invention to provide a method for the restoration of leached reservoirs.

A further object of the present invention is to provide a method for the restoration of leached reservoirs having high TDS levels in the fluids therein.

It is an additional objective of the present invention to provide a method for the restoration of a leached reservoir through the injection of a sulfate reducing bacteria into the reservoir to decrease the level of TDS present therein.

Other objects, aspects, and several advantages of the present invention will become apparent upon a further reading of this disclosure and the appended claims.

It has now been found that the objects of the present invention can be attained by injecting a sulfate reducing bacteria into an underground reservoir which has been leached of its recoverable uranium.

In the operation of the present method, the sulfate reducing bacteria consume the undesirable sulfate ions present in the reservoir and generate hydrogen sulfide gas ($H_2S$). The hydrogen sulfide is generally present originally in an underground uranium bearing reservoir. Hydrogen sulfide, a weak dibasic acid, is a strong reducing agent and reacts with certain soluble contaminants such as iron, molybdenum, uranium, and vanadium to reduce their oxidation state and produce insoluble compounds. This reduces the TDS level of the reservoir fluid. Other soluble cations also react with hydrogen sulfide to produce insoluble sulfide salts which further reduces the TDS level of the reservoir fluid.

It is important that the sulfate reducing bacteria have both carbon and nutrient sources for growth. For certain bacteria, soluble bicarbonate and carbonate ions as well as solid carbonates provide the carbon source. Ammonium, nitrite, and nitrate ions are the nitrogeneous nutrients. Such bacteria are classified as autotrophic organisms.

It is known that there are species of bacteria present in seawater, fresh water and soils which utilize sulfate ions in their respiration processes. The organisms are of the genus Desulforvibrio. The species type Desulforvibrio desulfuricans achieves large scale reduction of sulfate ions to sulfide. It was also previously reported that Desulforvibrio growth can be effected in an inorganic medium if there is a source of carbon.

The carbon sources for the bacteria are not limited to the mass of carbonate species externally added to the reservoir fluid during the uranium solution mining operation. Solid carbonates in the reservoir are available directly and indirectly to the bacteria. The indirect source arises from the uranium oxidation wherein other minerals such as sulfides are also oxidized. For example, the oxidation of molybdenite or jordisite ($MoS_2$) and pyrite or marcasite follows the stoichiometric equations:

$$MoS_2 + 9/2\ O_2 + 3H_2O \rightarrow MoO_4^{-2} + 2SO_4^{-2} + 6H^+$$

$$FeS_2 + 15/4\ O_2 + 7/2\ H_2O \rightarrow Fe(OH)_3 + 2SO_4^{-2} + 4H^+$$

If the leach solution is undersaturated in carbonate species, the hydrogen ions generated in these oxidation reactions will react with solid carbonates present in the ore body to form soluble carbonate species. Using solid calcium and magnesium carbonates as examples, the stoichiometry for bicarbonate ion generation is:

$$CaCO_3 + H^+ \rightarrow Ca^{+2} + HCO_3^-$$

$$MgCO_3 + H^+ \rightarrow Mg^{+2} + HCO_3^-$$

which thus provides a soluble carbon source in the reservoir fluid for the growth of bacteria.

The bacteria are mobile organism which will disperse throughout the contaminated region of the reservoir. The extent of the dispersion is limited by the availability of the nitrogeneous nutrients and sulfate ions. Significant quantities of these species are restricted to the contaminated reservoir region.

It has been found that the high bicarbonate levels in a leached reservoir will sustain a genus Desulforvibrio organism and that the hydrogen sulfide consuming reactions are compatible with continued growth of the organism. When the supply of bicarbonate, carbonate, and/or sulfate is exhausted or falls to a near zero level, the bacteria will expire providing a self-terminating method for the in situ reservoir restoration. At the time of bacteria expiration, the high TDS level will substantially be reduced due to the consumption by the bacteria of soluble nitrogen species, bicarbonate, carbonate, and sulfate ions which along with chloride ions are the major constituents of the high TDS level. In addition, the bacteria generated hydrogen sulfide will continue to react in the absence of the bacteria to further reduce the oxidation state of the reservoir fluid and the concentrations of other soluble species.

The following comparative example is shown to illustrate the effective operation of the method described herein. A comparison between the use of bacteria and its non-use is shown.

An ore body 35,000 square feet in area and averaging 20 feet in thickness lies at an average depth of 400 feet below the surface of the earth. The ore is primarily an unconsolidated sandstone containing approximately 15 weight percent carbonates, 2 weight percent iron sulfide, and 1 weight percent organic carbon. The total uranium content of the ore averages 0.06 percent which is primarily uraninite.

Thirty-two wells are drilled into the ore body in an array forming twelve five spot patterns. The wells are completed in only the mineralized zone which is vertically isolated by low permeability strata above and below. Prior to initiation of the uranium leaching operation, all wells are pumped to remove sand and drilling debris. Subsequently, samples of the native water of the mineralized zone are obtained from all wells and analyzed for chemical composition. Average values are shown in column 3 of the Table and define the baseline, or original conditions of the reservoir.

Because of the high carbonate content of the reservoir, an alkaline leaching process is utilized rather than an acid leach. During the leaching process which continues for eighteen months an ammonia bicarbonate enriched leachant is cycled through the formation. An oxidant is injected into the twenty injection wells along with the leachant. As the fluid travels through the formation, the oxidant reacts with solid uranium, sulfides, and other oxidizable species to produce soluble and insoluble reaction products. The soluble products dissolve in the leachant and are produced at 12 production wells, the uranium content of the leachant is stripped on a uranium specific ion exchange resin, the ammonia bicarbonate, and oxidant concentrations are restored, and the leachant is reinjected into the formation. During this continuous cycling of leachant, no significant quantities of soluble species other than uranium are stripped from the leachant, and the anion donor on the ion exchange resin, chloride, is added to the leachant. Thus, the concentrations of soluble species other than uranium in the leachant steadily increase during the operation and are limited only by their saturation or solubility maximums. At conclusion of the leaching operation, the perturbed reservoir fluid, i.e., the leachant, is analyzed and found to have the composition shown in column 4 of the Table. A comparison of columns 3 and 4 of the Table clearly shows the magnitude of the perturbation inflicted upon the reservoir fluid. Regulatory agencies constraints require that this perturbation be reduced to near zero prior abandonment of the site.

A test, at a near identical site in the same ore body approximately 1,000 feet removed from the present site (edge to edge), characterizes the reservoir behavior when no external restoration efforts are attempted. Operations at this site are also conducted for eighteen months under identical operating conditions. The initial and final reservoir fluid compositions are within five percent of those of the present site. At conclusion of the leaching operation all wells are shut in for fourteen months. During this period only the naturally occurring processes within the reservoir interact with the perturbed reservoir fluid. At the end of this period three wells are reactivated and sufficient fluid pumped from the reservoir to permit acquisition of representative reservoir fluid samples. Averages of analyses of these samples are shown in column 5 of the Table. Within experimental accuracy, only the decrease in uranium concentration occurs during this period.

A culture of Desulfivibrio desulfurican bacteria is prepared in a medium consisting of the perturbed reservoir fluid and sodium lactate which is added to accelerate growth. Portions of the culture are continuously introduced into each of the twenty injection wells for twelve hours. During this period, fluid is removed from the reservoir via the twelve production wells, innoculated with the culture, and returned to the reservoir via the injection wells. The flow rate is sufficiently low as to minimize the shear forces exerted on the bacteria and, hence, their destruction. During the next four months, the wells are periodically sampled and the bacteria population monitored. At the end of this period reservoir fluid samples are obtained from several wells and analyzed. A noticeable hydrogen sulfide odor is observed with these samples which was absent during the leaching operation. The results of the chemical analyses are shown in column 6 of the Table. Direct appraisal of the effectiveness of the bacteria is made by comparing columns 5 and 6 of the Table. Resultant from the bacterial action, drastic reductions in the ammonia, bicarbonate, calcium, magnesium, molybdenum, sodium, and sulfate concentrations as well as the TDS level have occurred.

Ammonia is consumed by the bacteria as both a nutrient and energy source. Similarly, bicarbonate is a carbon source. Calcium, magnesium, and sodium concentration reductions result from exchange with clay bound ammonium ions which are consumed by the bacteria and the solubility limitations of their respective sulfite and sulfide forms. The bacteria generated hydrogen sulfide sufficiently lowers the oxidation state of the reservoir so that molybdenum and uranium are reduced to unsoluble forms.

For this example, complete restoration of the reservoir fluid is not achieved and additional treatment is required. However, major TDS components, namely, ammonia, bicarbonate, and sulfate, are removed. Conventional recovery of the remaining species such as calcium, sodium and chloride by such methods as ion exchange is far less difficult and expensive in the absence of these other species than in their presence.

While the example illustrates the use of a Desulfivibrio desulfurican bacteria strain, it should be understood that other similar sulfate reducing strains such as Vibrio are within the scope of the present invention.

The present invention has been described herein with reference to particular embodiments. Therefore, it will be appreciated by those skilled in the art, however, that various changes and modifications can be made therein without departing from the scope of the invention as presented.

I claim:

1. A method for the restoration of an underground reservoir subsequent to solution mining of a mineral from a subterranean formation containing said mineral which comprises introducing a sulfate reducing bacteria into said reservoir.

2. The method of claim 1 wherein said sulfate reducing bacteria is of the genus Desulforvibrio.

3. The method of claim 1 wherein said sulfate reducing bacteria is of the genus Vibrio.

4. The method of claim 1 wherein said reservoir has been leached with an alkaline leach solution.

5. The method of claim 1 wherein said reservoir has been leached with an acidic leach solution.

6. The method of claim 1 wherein said mineral is selected from the group comprising uranium, copper, nickel, vanadium, molybdenum, silver, rhenium and selenium.

* * * * *

UNITED STATES PATENT OFFICE
CERTIFICATE OF CORRECTION

PATENT NO. : 4,108,722  
DATED : August 22, 1978  
INVENTOR(S) : Dennis E. Stover Page 1 of 2

It is certified that error appears in the above-identified patent and that said Letters Patent are hereby corrected as shown below:

The attached page was omitted from the patent. Please insert at Col. 4, line 10.

Signed and Sealed this

Twenty-fifth Day of September 1979

[SEAL]

Attest:

LUTRELLE F. PARKER

*Attesting Officer*  *Acting Commissioner of Patents and Trademarks*

ANALYSIS OF MAJOR DISSOLVED SOLIDS COMPONENTS IN RESERVOIR FLUID

| 1 | 2 | 3 | 4 | 5 | 6 |
|---|---|---|---|---|---|
| Species | Units | Prior to Initiation of In Situ Alkaline Uranium Leaching | At Completion (18 months operation) of In Situ Alkaline Uranium Leaching | After 14 Month Shut In Of Site (Post Leaching) | After 4 Month Shut I With Bacteri |
| pH | | 7.4 | 7.0 | 7.2 | 7.0 |
| Ammonia | ppm | <1 | 145 | 130 | <1 |
| Bicarbonate | ppm | 182 | 471 | 465 | 125 |
| Calcium | ppm | 43 | 725 | 730 | 120 |
| Chloride | ppm | 243 | 950 | 946 | 930 |
| Magnesium | ppm | 10 | 100 | 95 | 35 |
| Molybdenum | ppm | <1 | 22 | 18 | <1 |
| Sodium | ppm | 187 | 578 | 580 | 220 |
| Sulfate | ppm | 42 | 2005 | 1980 | <20 |
| Uranium | ppm | <1 | 10 | <1 | <1 |
| Total Dissolved Solids | ppm | 742 | 5020 | 4980 | 1500 |